United States Patent [19]

Kawamura et al.

[11] Patent Number: 5,652,147

[45] Date of Patent: Jul. 29, 1997

[54] METHOD OF MEASURING CONCENTRATION OF POLYMERIZATION INHIBITOR CONTAINED IN FLUORINE-CONTAINING OLEFINIC MONOMER AND METHOD OF POLYMERIZING FLUORINE-CONTAINING OLEFINIC MONOMER COMPRISING THE MEASUREMENT METHOD

[75] Inventors: Takuo Kawamura; Shigeru Ichiba; Tomizo Soda, all of Osaka, Japan

[73] Assignee: Daikin Industries, Ltd., Osaka, Japan

[21] Appl. No.: 617,776

[22] PCT Filed: Sep. 19, 1994

[86] PCT No.: PCT/JP94/01536

§ 371 Date: Mar. 20, 1996

§ 102(e) Date: Mar. 20, 1996

[87] PCT Pub. No.: WO95/08762

PCT Pub. Date: Mar. 30, 1995

[30] Foreign Application Priority Data

Sep. 20, 1993 [JP] Japan ..................... 5-232637

[51] Int. Cl.$^6$ ..................... G01N 33/44; C07C 17/42; C07C 17/00
[52] U.S. Cl. ..................... 436/142; 436/139; 436/164; 436/167; 436/178; 570/103; 570/138
[58] Field of Search ..................... 570/103, 138; 436/139, 142, 164, 167, 177, 178, 183, 171

[56] References Cited

U.S. PATENT DOCUMENTS

| | | |
|---|---|---|
| 2,407,405 | 2/1946 | Dietrich. |
| 3,695,847 | 10/1972 | Hirschfeld ..................... 436/142 |

FOREIGN PATENT DOCUMENTS

| | | |
|---|---|---|
| 4535795 | 11/1970 | Japan. |
| 481115 | 1/1973 | Japan. |
| 4834399 | 10/1973 | Japan. |
| 5426918 | 9/1979 | Japan. |

OTHER PUBLICATIONS

J.G. Kirchner et al. *Anal. Chem.* 1951, 23, 420–425.
A.A. Belyakov *Chem. Abstr.* 1961, 55, 24396d.
Y. Watanabe *Chem. Abstr.* 1963, 58, 11405e.
M.G. Manson et al. *J. Chem. Phys.* 1973, 59, 1092–1098.

*Primary Examiner*—Arlen Soderquist
*Attorney, Agent, or Firm*—Birch, Stewart, Kolasch & Birch, LLP

[57] ABSTRACT

There is provided a precisely quantitative measurement method of a hydrocarbonaceous polymerization inhibitor component in a fluorine-containing olefinic monomer, which inhibitor component is contained in the monomer in such a trace amount that it cannot be detected by a gas chromatography. In the method, an ultraviolet absorption spectrum of a concentrated sulfuric acid is measured after it is contacted with the fluorine-containing olefinic monomer and the concentration of the polymerization inhibitor is obtained based on an absorbance of the spectrum and a calibration curve which has been beforehand obtained.

8 Claims, 4 Drawing Sheets

5,652,147

METHOD OF MEASURING CONCENTRATION OF POLYMERIZATION INHIBITOR CONTAINED IN FLUORINE-CONTAINING OLEFINIC MONOMER AND METHOD OF POLYMERIZING FLUORINE-CONTAINING OLEFINIC MONOMER COMPRISING THE MEASUREMENT METHOD

TECHNICAL FIELD

The present invention relates to a quantitatively measuring method of a trace amount of a component contained in a fluorine-containing olefinic monomer gas. Particularly, the present invention relates to a method of measuring a concentration of a polymerization inhibitor (or a polymerization preventive agent), especially of a trace polymerization inhibitor, remaining in a fluorine-containing olefinic monomer after it has been separated from the polymerization inhibitor and purified.

In addition, the present invention also relates to a method of polymerizing a fluorine-containing olefinic monomer comprising a concentration measurement step of the polymerization inhibitor by such a measurement method.

BACKGROUND ART

Fluorine-containing olefinic monomers, in particular tetrafluoroethylene (which is hereinafter referred to as "TFE") and chloro-trifluoroethylene (which is hereinafter referred to as "CTFE") are industrially important chemicals as a starting material for the production of a polymer of such a single monomer or a copolymer of such a monomer with another monomer or as an intermediate product for the production of various chemicals. Since TFE and CTFE have so low boiling points as −76.3° C. and −27.9° C. respectively, they are usually stored under pressure. Because of their high reactivities, they are ready to polymerize even in the presence of a trace amount of oxygen. In order to prevent such polymerization of the monomer during its storage, it has been known that a polymerization inhibitor (polymerization preventive agent) is added to the monomer (see, for example, U.S. Pat. No. 2,407,405).

As such a polymerization inhibitor, terpene compounds such as dipentene, terpinolene, p-cymene, α-pinene, p-menthane and so on are concretely exemplified. Because of easy handling and commercial availability, a mixture of such terpene compounds is usually used. A composition of a terpene polymerization inhibitor mixture is shown in Table 1 below which is commercially available:

TABLE 1

| Component | Product A | Product B | Product C |
|---|---|---|---|
| α-pinene | 4.0% | 5.0% | 3.1% |
| camphene | 3.6 | 3.6 | 3.4 |
| β-pinene | 1.3 | 0.2 | 0.5 |
| α-terpinene | 28.4 | 29.5 | 29.8 |
| dipentene | 14.6 | 11.4 | 18.5 |
| γ-terpinene | 16.6 | 17.5 | 14.9 |
| isoterpinolene | 12.7 | 9.6 | 7.9 |
| terpinolene | 6.4 | 13.8 | 10.6 |
| others | 12.4 | 4.0 | 11.3 |

Product A: Terpene mixture commercially available from Arakawa-Chemial as trade name of Terpene-B
Product B: Terpene mixture commercially available from Nippon-Terpene as trade name of Dipenten-T
Product C: Terpene mixture commercially available from Yasuhara-Yushi as trade name of Dipenten In order to use the stored monomer for a certain intended object such as polymerization thereof, it is required to remove the polymerization inhibitor of the terpenes which has been added to the monomer. For example, the monomer must be separated from the polymerization inhibitor and purified by treatment such as distillation, absorption or adsorption (for example, adsorption with silica gel). In such a case, if the separation of the polymerization inhibitor is insufficient or if a remaining amount of the polymerization inhibitor in the monomer fluctuates, the following disadvantages occur upon the polymerization of the monomer: consumption increase of a polymerization initiator, polymerization period increase due to reduction of polymerization reaction rate, decrease of polymer yield and property fluctuation of produced polymer. Therefore, the monomer is used as, for example, a polymerization starting material after the polymerization inhibitor has been removed from the monomer by a multistage separation-purification.

For the production of a polymer from a single kind monomer or a copolymer comprising the monomer, it is firstly desired to make a monomer quality uniform from a viewpoint of polymerization stability while polymerization conditions (in particular, a pressure and a temperature of a polymerization vessel) should be controlled and thus polymer property uniformity of the resulted polymer should be intended.

The fluorine-containing monomer is introduced into a polymerization vessel generally in a gas form for the polymerization thereof. For composition analysis of the gas monomer, a gas chromatography (which is hereinafter referred to as GC) is generally used. However, even though a flame ionization detector (which is hereinafter referred to as FID) providing the best sensitivity for the analysis of hydrocarbonaceous organic compounds is employed, a detection lower limit of terpenes as whole is about a few ppm for the case in which the polymerization inhibitor to be analyzed is a mixture of isomers as a terpene mixture since each compound of the terpenes is of a low concentration in spite that a concentration of the total terpenes is relatively large.

Generally, a concentration of the terpenes as a whole and also a concentration of each terpene compound in the monomer for the polymerization must be considerably lower than the detection lower limit of the GC with the FID after it has been purified, and it is therefore impossible to control a quality of a feedstock with the concentration of the remaining polymerization inhibitor in the feedstock using the GC. So the remaining polymerization inhibitor in a trace amount affects a polymerization step of the monomer, which is one of reasons why polymerization conditions are not stabilized. Although extensive maintenance and control of the polymerization step have been carried out from various viewpoints, they have not overcome the problems such as the fluctuation of the produced polymer properties.

DISCLOSURE OF THE INVENTION

The present inventors have made extensive studies on a method of quantitatively measuring a trace amount of a polymerization inhibitor component remaining in a fluorine-containing olefinic monomer (usually in the form of gas) of which concentration is below a detection lower limit of GC, and found that the above problems are overcome by contacting the fluorine-containing olefinic monomer gas such as TFE or CTFE with a concentrated sulfuric acid followed by measuring an ultraviolet (UV) absorption spectrum of the concentrated sulfuric acid, and then quantitatively determining a concentration of the trace polymerization inhibitor remaining in the monomer based on an absorbance of the absorption spectrum, which leads to the present invention.

In the first aspect, the present invention provides a method of measuring a concentration of a trace polymerization inhibitor, particularly of terpene compounds, contained in a fluorine-containing olefinic monomer as a total concentration of the terpene compounds or a concentration of each terpene compound characterized in that the monomer is contacted with a concentrated sulfuric acid followed by measuring an ultraviolet absorption spectrum of the concentrated sulfuric acid, and then the concentration of the polymerization inhibitor in the monomer is determined from an absorbance of the absorption spectrum based on a calibration curve beforehand obtained at a predetermined wavelength which curve defines a relationship between the absorbance of the ultraviolet absorption spectrum and the concentration of the polymerization inhibitor.

When the present method is applied to a measuring method of a polymerization inhibitor concentration in a fluorine-containing olefinic monomer during the polymerization of the monomer, control of the polymerization inhibitor concentration in the monomer is easily carried out so that the concentration can be kept constant, which leads to stable polymerization.

In the second aspect, the present invention thus provides a process of polymerizing a fluorine-containing olefinic monomer comprising the steps of:

removing a polymerization inhibitor from the fluorine-containing olefinic monomer so as to obtain a purified fluorine-containing olefinic monomer, measuring a concentration of the polymerization inhibitor remaining in the purified fluorine-containing olefinic monomer by the method of the first aspect of the present invention, namely by contacting the purified fluorine-containing olefinic monomer which contains the polymerization inhibitor with a concentrated sulfuric acid and determining the concentration of the polymerization inhibitor based on an ultraviolet absorption spectrum of thus contacted concentrated sulfuric acid, and then polymerizing the monomer.

DETAILED DESCRIPTION OF THE INVENTION

Figure 1:
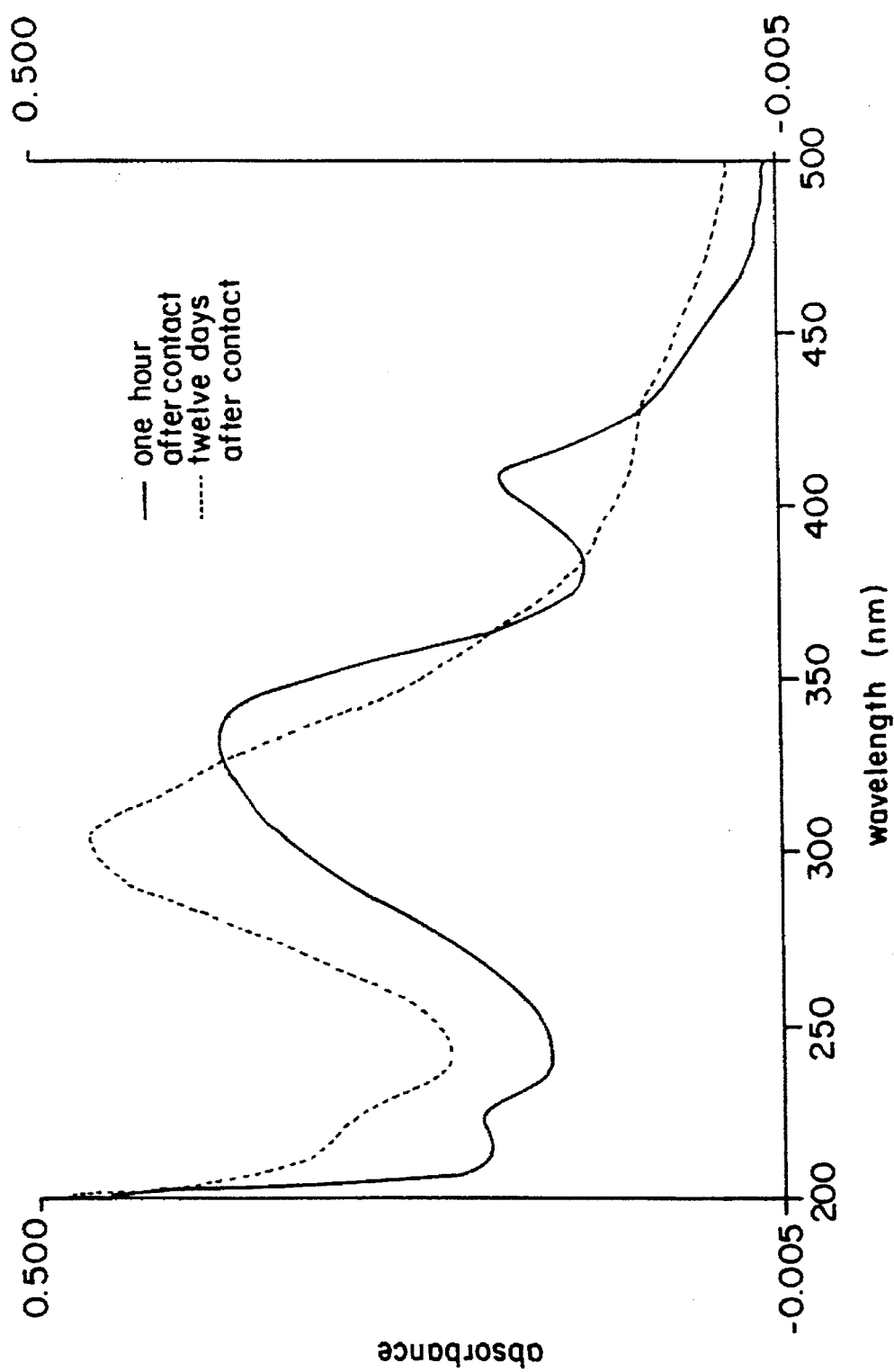
FIG. 1 shows one example of an ultraviolet absorption spectrum change regarding an elapsing period after absorption treatment with a concentrated sulfuric acid of a fluorine-containing olefinic monomer (concretely, TFE) which contains terpenes (commercial product A in Table 1) (one hour and twelve days after the contact treatment).

Not bound by any theory, in the present invention, by contacting the fluorine-containing olefinic monomer, which contains the polymerization inhibitor in a trace amount, usually in the form of gas with the concentrated sulfuric acid, the polymerization inhibitor(s) which shows specific UV absorption is absorbed (or taken) into the concentrated sulfuric acid in some form, for example as it is, or in a form reacted with the concentrated sulfuric acid, or in other forms. Such contact is carried out in a conventional gas-liquid contacting apparatus. For example, the contact may be carried out by bubbling the fluorine-containing olefinic monomer gas in the concentrated sulfuric acid. Alternatively, a so-called gas absorber or gas sampler (gas collector) may be used. In this case, it is preferable that a tube through which the fluorine-containing olefinic monomer gas is supplied into the concentrated sulfuric acid has, at its tip, a porous member (for example a glass filter) so that the monomer is introduced into the concentrated sulfuric acid as fine bubbles and gas-liquid (concentrated sulfuric acid) contact efficiency is improved. In order to improve the absorption efficiency, such contact is preferably carried out using multiple stages in series.

It is, of course, possible to contact the monomer as a liquid with the concentrated sulfuric acid under a high pressure. In this case, the pressure should be reduced after the contact so as to vaporize and remove the fluorine-containing olefinic monomer.

The polymerization inhibitors to which the present concentration measuring method can be applied are so-called terpene compounds and any mixture thereof, and particularly those used for the fluorine-containing olefinic monomer. Concretely, dipentene, terpinolene, p-cymene, α-pinene, p-menthane, α-terpinene, β-pinene, and isoterpinolene can be exemplified.

The fluorine-containing olefinic monomers to which the present concentration measuring method can be applied are ethylene derivatives containing a fluorine(s). Concretely, tetrafluoroethylene (TFE) and chloro-trifluoroethylene (CTFE) can be exemplified. Also, the method is applied to a mixture thereof.

Regarding the concentration of the polymerization inhibitor which can be measured by the present measuring method is not specifically limited, but the concentration of the polymerization inhibitor in the fluorine-containing olefinic monomer is usually in the range of about 0.1 ppb to 200 ppm and preferably about 0.01 ppm to 100 ppm.

However, when an amount of the fluorine-containing olefinic monomer which is subjected to the contact treatment is increased, an amount of the absorbed polymerization inhibitor is increased so that it is increased beyond a detection limit of the present measuring method (namely, the concentration of the polymerization inhibitor in the concentrated sulfuric acid becomes increased). Then, even though the polymerization inhibitor concentration in the monomer is less beyond the above mentioned ranges, it is, of course, possible to measure the polymerization inhibitor concentration by the present method. Also, when the polymerization inhibitor concentration is larger beyond the above mentioned ranges, the present method can be carried out with reduction of an amount of the .polymerization inhibitor absorbed by the concentrated sulfuric acid by shortening a contact period and/or with diluting the fluorine-containing olefinic monomer by a proper material, for example an inert gas so that the polymerization inhibitor concentration is adjusted within the above mentioned preferable concentration ranges.

In the present method, a so-called concentrated sulfuric acid can be used as the concentrated sulfuric acid (usually its concentration is not less than 90% by weight, and the balance is substantially water), and a concentrated sulfuric acid of a commercial guaranteed reagent grade (for example having a concentration of 95% by weight) can be used. However, the concentrated sulfuric acid in the present invention is not limited to those acids, a sulfuric acid of a less concentration may be used. In such case, the following should be considered: When the concentration is reduced and the water content is increased, solubility (or absorption ratio) of the polymerization inhibitor into the sulfuric acid is decreased; and even though the same amount of the polymerization inhibitor is dissolved, the absorbance is reduced as the concentration of the sulfuric acid is reduced. Thus, when the concentration of the sulfuric acid is not less than 70% by weight, it can be used as the concentrated sulfuric acid of the present method depending on the concentration of the polymerization inhibitor in the monomer. In a more preferable embodiment, the sulfuric acid of which concentration is at least 90% by weight is used (the balance is water is used). For example, when the concentration of the polymerization inhibitor in the monomer is relatively large, the sulfuric acid of which concentration is relatively smaller may be used.

A temperature at which the contact treatment of the fluorine-containing olefinic monomer with the concentrated sulfuric acid is not specifically limited, but the contact may be generally carried out at around room temperature. However, the contact can be carried out also at a higher or a lower temperature. Since the contact temperature affects solubility of the polymerization inhibitor, viscosity of the concentrated sulfuric acid, a transfer rate of the polymerization inhibitor from the monomer to the concentrated sulfuric acid and so on, it should be noted that an absorption extent of the polymerization inhibitor depends on the contact temperature.

In the present method, the ultraviolet absorption spectrum of the contacted sulfuric acid is measured. This is a well known method which is used for the ultraviolet absorption spectrometry. In this measurement, a particularly preferable ultraviolet wavelength is in the range of 230 to 500 nm, more preferably 250 to 370 nm, and absorbances at any wavelength within such ranges may be used for carrying out the present method. The most preferable wavelength range is 300 to 330 nm, and a wavelength within this range has a relatively small effects with an elapsing time after the contact treatment before the spectrum absorbance measurement. This is because it has been found that the absorbance does not change so much at a wavelength within that range (i.e. a stable range) even after a considerable long time has passed after the contact treatment.

Comparing thus obtained absorbance with a calibration curve which has been beforehand obtained, a concentration of the polymerization inhibitor in the concentrated sulfuric acid is determined firstly, which concentration is finally converted to the polymerization inhibitor concentration in the monomer under considerations of an amount of a sample which has been subjected to the contact treatment and so on.

Establishment of the calibration curve is a well known technique which is usually used in various analysis fields, and the calculation of the polymerization inhibitor concentration in $H_2SO_4$ based on the calibration curve and the conversion to the final polymerization inhibitor concentration in the monomer are also well known techniques which are generally carried out in the analysis fields. Therefore, no additional detailed explanation would be required for such well known techniques.

For example, the establishment of the calibration curve may be carried out by measuring ultraviolet spectrum absorptions as to concentrated sulfuric acids which have been beforehand prepared to have various known polymerization inhibitor concentrations and plotting a relationship between absorbances of the spectrum absorptions and the known polymerization inhibitor concentrations. According to the studies of the inventors, during such establishment, since the absorbances may be changed with an elapsed period depending on the wavelength at which they are measured, a period after the absorption of the polymerization inhibitor before the measurement must be constant if they are changed. During the measurement which uses a wavelength range in which the absorbance changes little with the elapsing period, such period of the measurement does not have to be strictly constant.

As described above, such a wavelength range is 250 to 370 nm and preferably 300 to 330 nm for the terpene compounds and their mixtures as the polymerization inhibitor. In those ranges, even though the period after the contact treatment with the concentrated sulfuric acid before the measurement is changed more or less, the measured absorbance is not so changed and stable. For example, spectrum change with the elapsing period is shown in FIG. 1 in which the terpenes (commercial product A in Table 1) were used. As seen from FIG. 1, an optimum wavelength in this case is about 320 nm.

Figure 2:
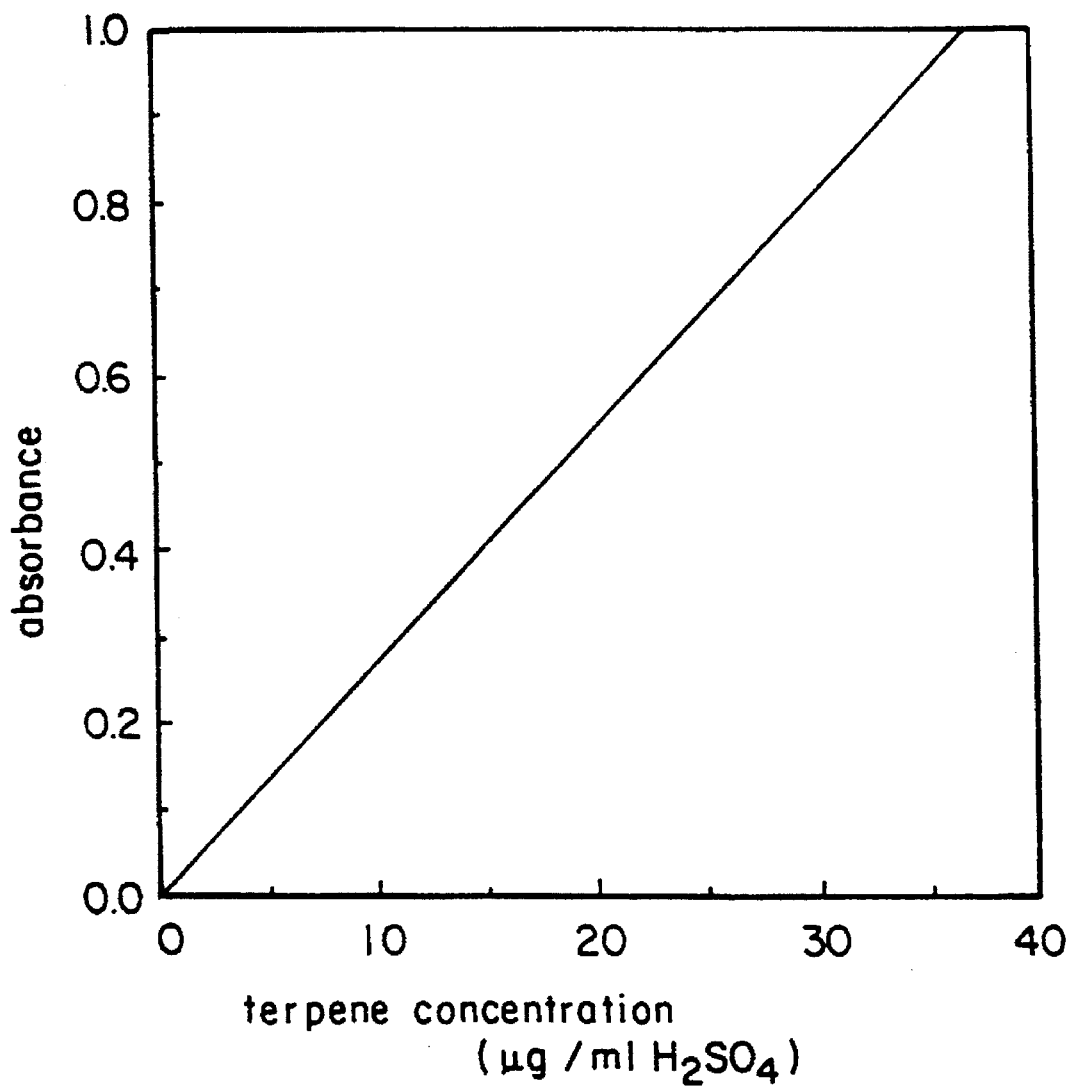
FIG. 2 shows one example of a calibration curve of the terpenes (commercial product A in Table 1) derived from absorbances at a wavelength of 320 nm.
Figure 3:
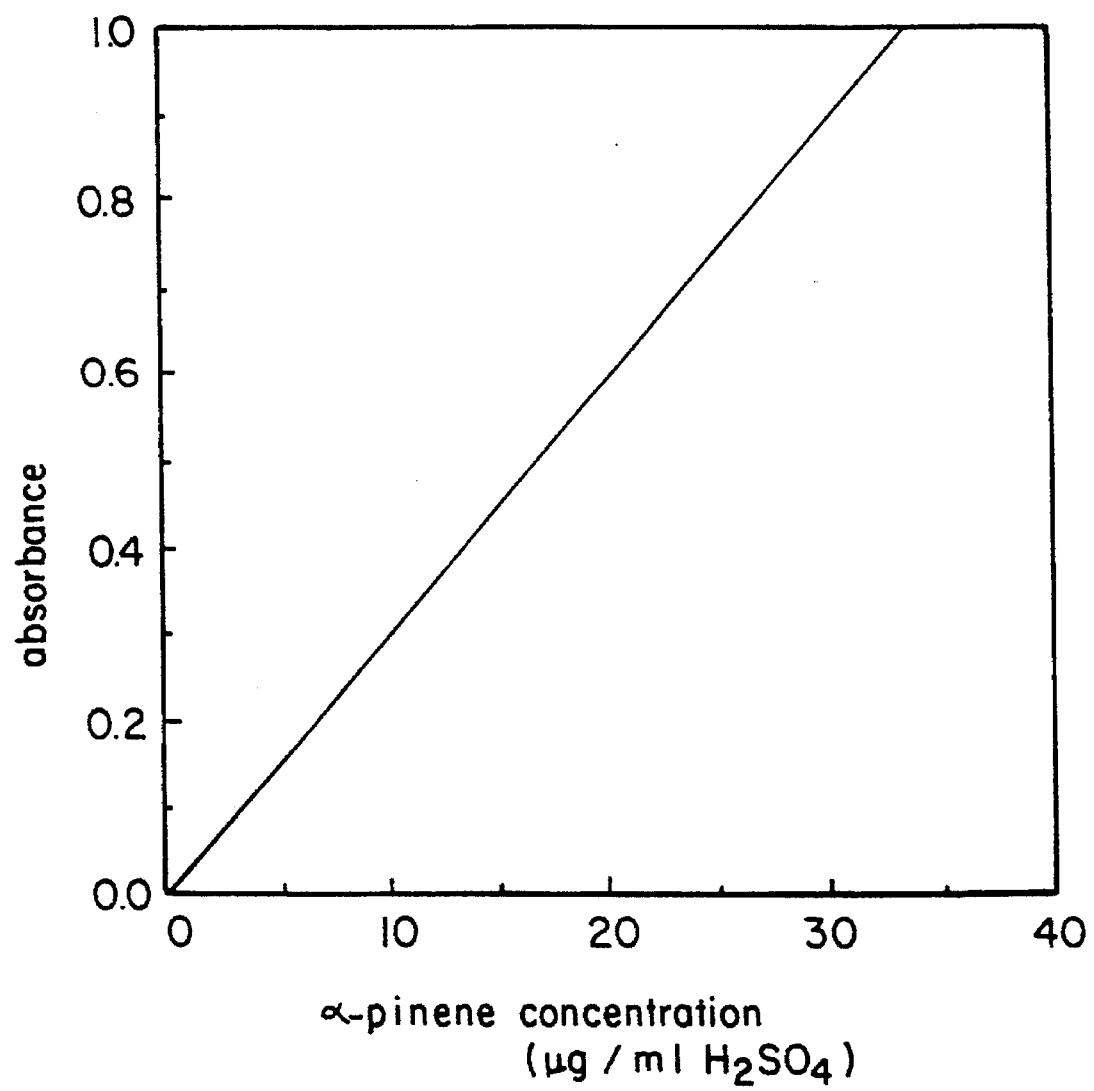
FIG. 3 shows one example of a calibration curve of α-pinene derived from absorbances at a wavelength of 320 nm.
Figure 4:
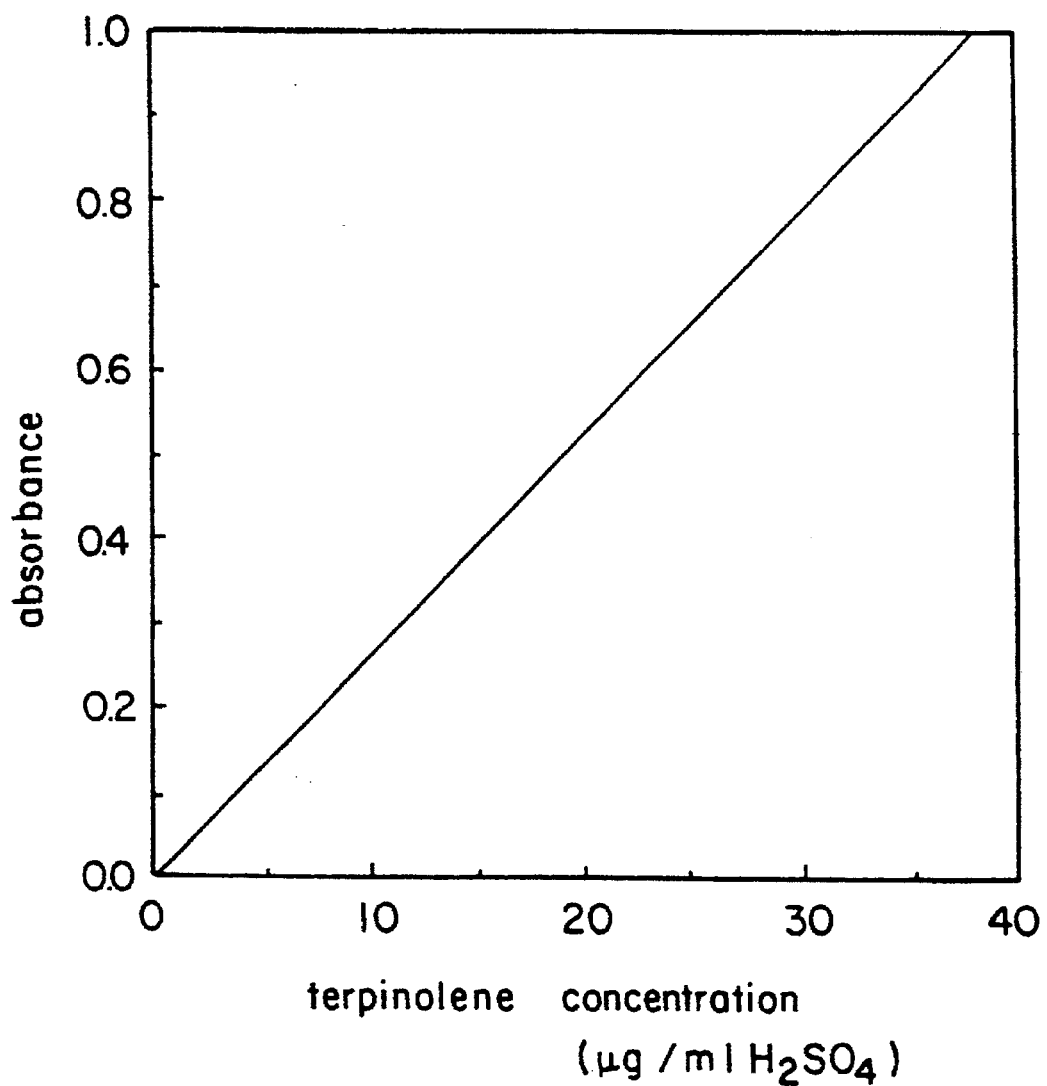
FIG. 4 shows one example of a calibration curve of terpinolene derived from absorbances at a wavelength of 320 nm.

Examples of calibration curves (graphs) using a wavelength of 320 nm for the terpenes (commercial product A in Table 1), α-pinene and terpinolene are shown in FIGS. 2, 3 and 4, respectively. In the graphs of the figures, the abscissa axis represents the polymerization inhibitor (such as the terpenes) concentration in the concentrated sulfuric acid ($\mu g/ml$-$H_2SO_4$) and the ordinate axis represents the absorbance at a wavelength of 320 nm. Thus, according to such calibration curve, the polymerization inhibitor concentration in the sulfuric acid is determined based on the measured absorbance at a correspponding wavelength. Then, the polymerization inhibitor concentration in the monomer is obtained based on that concentration and the amount of the monomer which has been subjected to the contact treatment.

The polymerization process to which the present polymerization process can be applied may be any polymerization process (or copolymerization process) in which the fluorine-containing olefinic monomer is used to which monomer the present polymerization inhibitor concentration measurement method can be applied. For example, the present process can be applied to the production process of producing a polytetrafluoroethylene as described in Japanese Patent Kokoku Publication (JP-B) Nos. 48-1115 or 48-34399.

In any polymerization process of the fluorine-containing olefinic monomer, the polymerization inhibitor concentration in the fluorine-containing olefinic monomer to be polymerized is measured according to the method of the first aspect of the present invention followed by the polymerization, or the polymerization is carried out while optionally measuring the polymerization inhibitor concentration according to the present invention. Concretely, when the polymerization inhibitor concentration is not less than a predetermined standard level (for example 90 ppb for the polymerization of TFE) after the removal of the polymerization inhibitor, such monomer is not used for the polymerization and subjected to the polymerization inhibitor removal treatment again, or a supply of such monomer to the polymerization step is stopped if the measurement is carried during the polymerization.

As one concrete example, TFE is vapor-phase polymerized under a pressure of 3 to 10 atms at a temperature of 0° to 40° C. in the presence of water which contains a polymerization initiator. For such vapor-phase polymerization, the polymerization inhibitor concentration in TFE has been measured beforehand according to the present method for the measurement of the polymerization inhibitor concentration.

EXAMPLES

The present invention will be hereinafter described in detail with reference to Examples.

Example 1

After most terpenes were removed from TFE which contained the terpenes (commercially available product A in Table 1) with silica gel (concretely a glass column filled with the silica gel), 60 liters of the TFE was introduced at a flow rate of 3 l/min. into and sufficiently contacted with a concentrated sulfuric acid (7 ml, guaranteed grade, purity of not less than 95%, from Futaba Pure Chemical) contained in a gas sampler comprising a gas introduction tube which has a glass filter at its tip (volume of 30 ml, commercially available as "Bubbler" from Shibata Chemical) so that the terpenes were absorbed into the concentrated sulfuric acid (at room temperature).

After the contact treatment, the ultraviolet absorption spectrum of the concentrated sulfuric acid was measured (using an apparatus: U-3200 from Hitachi), and a terpene concentration in the monomer after the silica gel treatment was quantified based on the absorbance at 320 nm of the spectrum and the calibration curve shown in FIG. 2. The results are shown in Table 2.

In Table 2, "Collection Ratio" is defined as a ratio of "an amount of the polymerization inhibitor absorbed by the concentrated sulfuric acid which amount was calculated based on the measured concentration under the operation conditions of Example (namely, a total amount of the polymerization inhibitor which could be detected by the present measurment method)" to "an amount of the polymerization inhibitor which amount was obtained by contacting with the concentrated sulfuric acid so as to absorb substantially 100% of the polymerization inhibitor" (it has been experimentally confirmed that substantially all of the polymerization inhibitor could be absorbed by multistage gas samplers in series while depending on the polymerization inhibitor concentration). "Concentration" is a converted one to the polymerization inhibitor concentration in the monomer which has been contacted with the concentrated sulfuric acid (in Example, the concentration in the monomer after the silica gel treatment).

Example 2

The concentration measurement of Example 1 was repeated except that the TFE contained the terpenes (commercially available product A in Table 1) as the polymerization inhibitor at a different concentration, the terpenes were removed from the TFE by supplying it to a silica gel column (an iron column filled with the silica gel), and 720 liters of the TFE were supplied to the concentrated sulfuric acid of 7 ml contained in the gas sampler for the sufficient contact treatment.

After the treatment, the ultraviolet absorption spectrum of the concentrated sulfuric acid was measured and a terpene concentration in the TFE monomer after the silica gel column treatment (corresponding to "Concentration" in Table 2) was calculated based on the absorbance at 320 nm and the calibration curve shown in FIG. 2. The results are shown in Table 2.

Example 3

Example 1 was repeated except that the TFE contained $\alpha$-pinene as the polymerization inhibitor, and the terpene compound was removed with the silica gel followed by introducing 60 liters of the TFE into the concentrated sulfuric acid of 7 ml contained in the gas sampler for the sufficient contact treatment.

After the treatment, the ultraviolet absorption spectrum of the concentrated sulfuric acid was measured and an $\alpha$-pinene concentration in the TFE monomer after the silica gel treatment was quantified based on the absorbance at 320 nm and the calibration curve shown in FIG. 3. The results are shown in Table 2.

Example 4

Example 2 was repeated except that the TFE contained $\alpha$-pinene as the polymerization inhibitor, and $\alpha$-pinene was removed by supplying it to the silica gel column followed by introducing 720 liters of the TFE into the concentrated sulfuric acid of 7 ml contained in the gas sampler for the sufficient contact treatment.

After the treatment, the ultraviolet absorption spectrum of the concentrated sulfuric acid was measured and the terpene compound concentration contained in the TFE monomer after the silica gel column treatment was determined based on the absorbance at 320 nm and the calibration curve shown in FIG. 3. The results are shown in Table 2.

Example 5

Example 1 was repeated except that the TFE contained terpinolene as the polymerization inhibitor, and terpindene was removed with the silica gel followed by introducing 60 liters of the TFE into the concentrated sulfuric acid of 7 ml contained in the gas sampler for the sufficient contact treatment.

After the treatment, the ultraviolet absorption spectrum of the concentrated sulfuric acid was measured and the terpinolene concentration contained in the monomer after the silica gel treatment was determined based on the absorbance at 320 nm and the calibration curve shown in FIG. 4. The results are shown in Table 2.

Example 6

Example 2 was repeated except that the TFE contained terpinolene as the polymerization inhibitor, and terpinolene was removed by supplying it to the silica gel column followed by introducing 720 liters of the TFE into the concentrated sulfuric acid of 7 ml contained in the gas sampler for the sufficient contact treatment.

After the treatment, the ultraviolet absorption spectrum of the concentrated sulfuric acid was measured and the terpinolene concentration contained in the TFE monomer after the silica gel column treatment was determined based on the absorbance at 320 nm and the calibration curve shown in FIG. 4. The results are shown in Table 2.

Example 7

The concentration measurement of Example 1 was repeated except that CTFE was used which contained the terpenes (commercially available product A in Table 1) as the polymerization inhibitor, and the terpenes were removed with the silica gel, and 60 liters of the CTFE were supplied to the concentrated sulfuric acid of 7 ml contained in the gas sampler for the sufficient contact treatment.

After the treatment, the ultraviolet absorption spectrum of the concentrated sulfuric acid was measured and the terpene concentration contained in the CTFE monomer after the silica gel treatment was determined based on the absorbance at 320 nm and the calibration curve shown in FIG. 2. The results are shown in Table 2.

Example 8

Example 2 was repeated except that the CTFE was used which contained the terpenes (commercially available product A in Table 1) as the polymerization inhibitor, and the terpenes were removed by supplying it to the silica gel column followed by introducing 720 liters of the TEE into the concentrated sulfuric acid of 7 ml contained in the gas sampler for the sufficient contact treatment.

After the treatment, the ultraviolet absorption spectrum of the sulfuric acid was measured and the terpene concentration contained in the CTFE monomer after the silica gel column treatment was measured based on the absorbance at 320 nm and the calibration curve shown in FIG. 2. The results are shown in Table 2.

Example 9

Example 1 was repeated except that the CTFE contained α-pinene as the polymerization inhibitor, and the terpene compound was removed with the silica gel followed by introducing 60 liters of the CTFE into the concentrated sulfuric acid of 7 ml contained in the gas sampler for the sufficient contact treatment.

After the treatment, the ultraviolet absorption spectrum of the concentrated sulfuric acid was measured and the α-pinene concentration contained in the CTFE monomer after the silica gel treatment was determined based on the absorbance at 320 nm and the calibration curve shown in FIG. 3. The results are shown in Table 2.

Example 10

Example 2 was repeated except that the CTFE contained α-pinene as the polymerization inhibitor, and α-pinene was removed by supplying it to the silica gel column followed by introducing 720 liters of the CTFE into the concentrated sulfuric acid of 7 ml contained in the gas sampler for the sufficient contact treatment.

After the treatment, the ultraviolet absorption spectrum of the concentrated sulfric acid was measured and the terpene compound concentration contained in the monomer after the silica gel column treatment was determined based on the absorbance at 320 nm and the calibration curve shown in FIG. 3. The results are shown in Table 2.

Example 11

Example 1 was repeated except that the CTFE contained terpinolene as the polymerization inhibitor, and terpinolene was removed with the silica gel followed by introducing 60 liters of the CTFE into the concentrated sulfuric acid of 7 ml contained in the gas sampler for the sufficient contact treatment.

After the treatment, the ultraviolet absorption spectrum of the concentrated sulfuric acid was measured and the terpinolene concentration contained in the CTFE monomer after the silica gel treatment was determined based on the absorbance at 320 nm and the calibration curve shown in FIG. 4. The results are shown in Table 2.

Example 12

Example 2 was repeated except that the CTFE contained terpinolene as the polymerization inhibitor, and terpinolene was removed by supplying it to the silica gel column followed by introducing 720 liters of the CTFE into the concentrated sulfuric acid of 7 ml contained in the gas sampler for the sufficient contact treatment.

After the treatment, the ultraviolet absorption spectrum was measured and the terpinolene concentration contained in the CTFE monomer after the silica gel column treatment was determined based on the absorbance at 320 nm and the calibration curve shown in FIG. 4. The results are shown in Table 2.

TABLE 2

| Example | Monomer | Polymerization Inhibitor | Sample Amount (l) | Collection Ratio (%) | Concentration (ppb) |
|---|---|---|---|---|---|
| 1 | TFE | Terpenes | 60 | ≧99.5 | 120 |
| 2 | TFE | Terpenes | 720 | ≧70 | 0.8 |
| 3 | TFE | α-pinene | 60 | ≧99.5 | 213 |
| 4 | TFE | α-pinene | 720 | ≧70 | 1.1 |
| 5 | TFE | Terpinolene | 60 | ≧99.5 | 158 |
| 6 | TFE | Terpinolene | 720 | ≧70 | 2.3 |
| 7 | CTFE | Terpenes | 60 | ≧99.5 | 125 |
| 8 | CTFE | Terpenes | 720 | ≧70 | 1.0 |
| 9 | CTFE | α-pinene | 60 | ≧99.5 | 111 |
| 10 | CTFE | α-pinene | 720 | ≧70 | 1.7 |
| 11 | CTFE | Terpinolene | 60 | ≧99.5 | 177 |
| 12 | CTFE | Terpinolene | 720 | ≧70 | 1.2 |

Sample Temperature: 23° C., Sample Flow Rate: 3 liter/min.
Concentrated Sulfuric Acid Amount: 7 ml.

Example 13

A polymerization inhibitor was removed beforehand with silica gel from TFE monomer containing the terpenes as the polymerization inhibitor (commercial product A), and then a polymerization inhibitor concentration in the monomer was measured according to the present method, which was followed by polymerizing the TFE of which measured polymerization inhibitor concentration was not more then 90 ppb.

The measurement of the polymerization inhibitor concentration was carried out by introducing a TFE sample at 3 liters/min. for 20 minutes into a gas absorber which contained 7 ml of a concentrated sulfuric acid (97%) therein so as to absorb the terpenes and measuring the absorbance of the sulfuric acid at a wavelength of 320 nm.

One million parts by weight of deoxygenated pure water was charged into an autoclave made of stainless steel having a volume corresponding to two million parts by weight of water and inside air was replaced with nitrogen, which was followed by replacement of the nitrogen with the TFE of which polymerization inhibitor concentration had been confirmed to be not more than 90 ppb according to the present method. Then, 2.0 parts by weight of ammonium persulfate, 3.0 parts by weight of sodium sulfite and 1.0 part by weight of iron sulfate were added while keeping a temperature inside the autoclave at 10° C., and stirring was started. Thereafter, the TFE of which polymerization inhibitor concentration was not more than 90 ppb was pressed into the autoclave to reach a pressure of 8 atms and polymerized. During the polymerization, the TFE was continuously pressed into so as to keep the pressure at 8 atms. After five hours passed, stirring was stopped and then the pressure in the autoclave was decreased using a vacuum pump while unreacted TFE was recovered.

As a comparative example, prior art polymerization was carried out in which operation conditions were kept as predetermined without the measurement of the polymerization inhibitor concentration while assuming that the polymerization inhibitor has been removed to not more than a predetermined concentration, namely no measurement method according to the present invention was carried out.

Polymerization results are shown below:

|  | Polymer Average Molecular Weight | Molecular Weight Deviation |
|---|---|---|
| Example | $650 \times 10^4$ | $70 \times 10^4$ |
| Comparative Example | $730 \times 10^4$ | $20 \times 10^4$ |

The molecular weight was measured by the S.G. method.

We claim:

1. A method of measuring a concentration of a polymerization inhibitor contained in a fluorine-containing olefinic monomer characterized in that the fluorine-containing olefinic monomer containing the polymerization inhibitor is contacted with a concentrated sulfuric acid before an ultraviolet absorption spectrum of the concentrated sulfuric acid obtained by the contact is measured, and then the concentration of the polymerization inhibitor is quantitatively determined based on an absorbance of the measured spectrum.

2. The method according to claim 1 wherein the fluorine-containing olefinic monomer is tetrafluoroethylene.

3. The method according to claim 1 wherein the fluorine-containing olefinic monomer is chloro-trifluoroethylene.

4. The method according to claim 1 wherein the polymerization inhibitor is a terpene compound.

5. The method according to claim 4 wherein the polymerization inhibitor comprises at least one selected from the group consisting of α-pinene, α-terpinene and terpinolene.

6. The method according to claim 4 or 5 wherein the ultraviolet absorption spectrum is measured in the range of 250–370 nm.

7. The method according to claim 1 wherein the concentrated sulfuric acid has a purity of not less than 90% by weight.

8. A process of polymerizing a fluorine-containing olefinic monomer which contains a polymerization inhibitor after the polymerization inhibitor is removed from the fluorine-containing olefinic monomer comprising the steps of:

obtaining a purified fluorine-containing olefinic monomer by removing the polymerization inhibitor before polymerizing it, measuring a concentration of the polymerization inhibitor contained in the fluorine-containing olefinic monomer by contacting the purified fluorine-containing olefinic monomer with a concentrated sulfuric acid followed by measuring an ultraviolet absorption spectrum of the contacted sulfuric acid obtained with the contact and by quantitatively determining the concentration based on the ultraviolet absorption spectrum, polymerizing the monomer when the polymerization inhibitor concentration is not larger than a predetermined level as a result of the measurement step.

* * * * *